(12) United States Patent
Osucha et al.

(10) Patent No.: US 7,006,919 B2
(45) Date of Patent: Feb. 28, 2006

(54) REAL TIME CONTINUOUS ELEMENTAL MEASUREMENT OF BULK MATERIAL

(75) Inventors: Peter M. Osucha, Knoxville, TN (US); David K. Swindell, Knoxville, TN (US)

(73) Assignee: Energy Technologies, Inc., Knoxville, TN (US)

( * ) Notice: Subject to any disclaimer, the term of this patent is extended or adjusted under 35 U.S.C. 154(b) by 112 days.

(21) Appl. No.: 10/853,629

(22) Filed: May 25, 2004

(65) Prior Publication Data

US 2005/0004763 A1 Jan. 6, 2005

Related U.S. Application Data

(60) Provisional application No. 60/474,911, filed on Jun. 2, 2003.

(51) Int. Cl.
*G01N 23/222* (2006.01)

(52) U.S. Cl. .................. 702/2; 702/8; 702/26; 702/28

(58) Field of Classification Search .................. 702/2, 702/6, 8, 26, 28
See application file for complete search history.

(56) References Cited

U.S. PATENT DOCUMENTS

| 4,582,992 A | 4/1986 | Atwell et al. |
|---|---|---|
| 6,362,477 B1 | 3/2002 | Sowerby et al. |

*Primary Examiner*—Donald McElheny, Jr.
(74) *Attorney, Agent, or Firm*—Pitts & Brittian, P.C.

(57) ABSTRACT

Methods and apparatus for continuous real-time measurement of bulk material using gamma irradiation and neutron irradiation. A DGA device monitors bulk material flow and produces a spectrum that is compared to a baseline spectrum to produce a relative weight/impurity ratio. A PGNAA device monitors the same bulk material flow and produces a spectrum that is compared to a library of spectrums to produce a relative component ratio. The relative component ratio is processed with the relative weight/impurity ratio to produce an absolute weight and impurity value, which is then processed with the relative component ratio to produce absolute component, or analyte, values.

34 Claims, 4 Drawing Sheets

REAL TIME CONTINUOUS ELEMENTAL MEASUREMENT OF BULK MATERIAL

CROSS-REFERENCE TO RELATED APPLICATIONS

This application claims priority from Provisional Application Ser. No. 60/474,911, filed Jun. 2, 2003.

STATEMENT REGARDING FEDERALLY SPONSORED RESEARCH OR DEVELOPMENT

Not Applicable

BACKGROUND OF THE INVENTION

1. Field of Invention

The present invention relates to the use of radiation measurements for determining the elemental content of bulk material in an on-line process, and to the fusion of sensor technologies, specifically Prompt Gamma Neutron Activation Analysis (PGNAA) and Dual-Energy Gamma Attenuation (DGA), to make this measurement possible.

2. Description of the Related Art

Several technologies exist to determine the composition of bulk materials. Two that are specifically important to the present invention are Prompt Gamma Neutron Activation Analysis (PGNAA) and Dual-Energy Gamma Attenuation (DGA) analysis.

The PGNAA technique involves bombarding a bulk material sample with neutrons from a neutron emitter (typically Cf-252). The neutrons collide with atoms/elements in the sample, emitter housing, and/or an external moderator and are captured by the nuclei of atoms/elements present in the sample. The capture process often involves the release of gamma rays at energies specific to the captured atom/element. These gamma rays are detected typically by a scintillation crystal (typically NaI). The sum of the detected gamma energy at these specific energies is referred to as an energy spectrum. Analysis of the energy spectrum provides analytical information on the proportion of the various elements present in the bulk material.

Various PGNAA based sensor systems are known. One such analyzer is that described in U.S. Pat. No. 4,582,992, titled "Self-Contained, On-Line, Real-time Bulk Material Analyzer," issued to Atwell, et al., on Apr. 15, 1986, which uses PGNAA technology in an attempt to determine the elemental content of the bulk material. The described analyzer uses an arrangement of neutron sources and gamma ray detectors in an enclosed assembly to perform its analysis. Additionally, a similar device, described in U.S. Pat. No. 6,362,477, titled "Bulk Material Analyser for On-Conveyor Belt Analysis," issued to Sowerby, et al., on Mar. 26, 2002, uses PGNAA technology in a bulk material on-conveyor belt arrangement to analyze bulk material. Again, this analyzer uses a neutron source and gamma ray detectors in an enclosed assembly to perform its analysis.

The DGA analysis technique involves bombarding a bulk material with gamma rays from two gamma ray emitters of sufficiently different energies. The gamma rays interact with the bulk material resulting in the attenuation of the number of gamma rays transmitted through the bulk material. The gamma rays are typically detected by a scintillation crystal (typically NaI). The sum of these released gamma rays at these specific energies is referred to as an energy spectrum. The technology relies on the fact that elements with different atomic numbers attenuate gamma rays at specific energies in different ways. Thus, for low-energy gamma rays (i.e., those generated by a low energy gamma emitter such as Am-241), the attenuation of gamma rays is largely dependent on the atomic number of the atoms/elements present in the bulk material. For high-energy gamma rays (i.e., those generated by a high-energy gamma emitter such as Cs-137), attenuation is independent of the atoms/elements in the bulk material. Analysis of the energy spectrum leads to a determination of the bulk elemental composition of the bulk material.

DGA based sensors are known in the art. DGA devices are based on the premise that analyzed material will attenuate different energy gamma rays in fixed repeatable ways. A DGA device consists of a gamma energy source arrangement consisting of dual energy gamma emitters. The gamma emitters are chosen in such a way that the material to be analyzed will attenuate the different energy gamma rays in ways that are conducive to measuring one or more specific properties of the material being measured. One such application of DGA technology uses gamma ray sources to interrogate coal, with the assumption that the material that coal is composed of will attenuate the differing energy gamma rays to produce a measurement that is conducive to determining coal ash content and density.

BRIEF SUMMARY OF THE INVENTION

The present invention provides methods and apparatus for the measurement of the elemental content of bulk materials in a continuous fashion. The method, in one embodiment, includes the fusion of various technologies, particularly Prompt Gamma Neutron Activation Analysis (PGNAA) and Dual-energy Gamma Attenuation (DGA), to determine the elemental content of the measured material.

The apparatus, in one embodiment, includes a PGNAA device to determine relative elemental content of the bulk material, a DGA device to determine the relative material density and impurity content, and a computing/processing system for combining the data from each device into quantities representative of the material elemental content.

The DGA device monitors bulk material flow and produces a spectrum that is compared to a baseline spectrum to produce a relative weight/impurity ratio. The PGNAA device monitors the same bulk material flow and produces a spectrum that is compared to a library of spectrums to produce a relative component ratio. The relative component ratio is processed with the relative weight/impurity ratio to produce an absolute weight and impurity value, which is then processed with the relative component ratio to produce absolute component, or analyte, values. The outputs of the DGA device and the PGNAA device are received by a processor, which executes software for processing the outputs to produce the absolute values.

BRIEF DESCRIPTION OF THE SEVERAL VIEWS OF THE DRAWINGS

The above-mentioned features of the invention will become more clearly understood from the following detailed description of the invention read together with the drawings in which.

DETAILED DESCRIPTION OF THE INVENTION

A measurement system for continuous real-time measurement of bulk material is disclosed. The measurement system is shown as item 10 on the figures.

Figure 1:
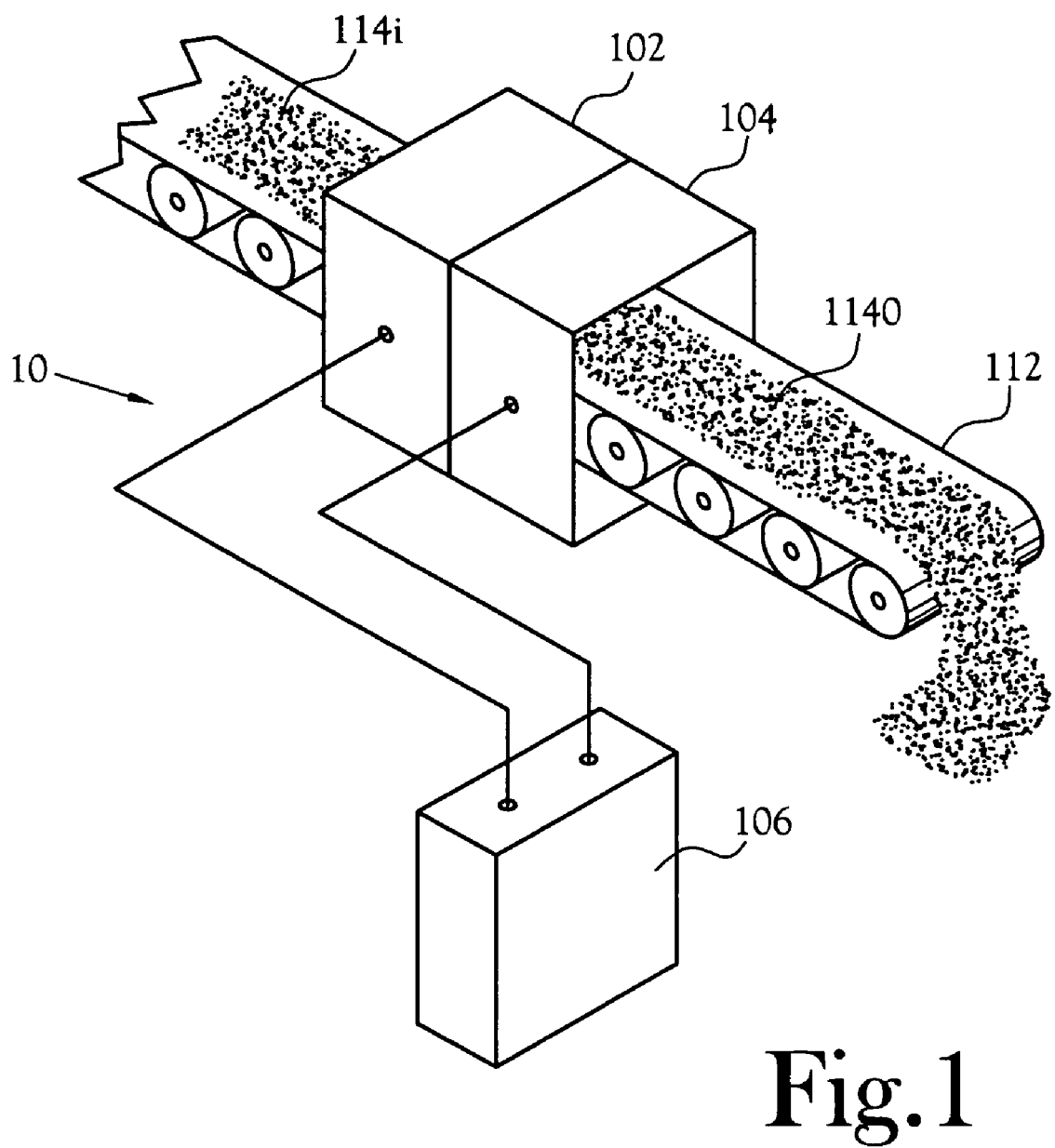
FIG. 1 is a pictorial view of one embodiment of the apparatus.

FIG. 1 illustrates one embodiment of the measurement system 10 as it is used with a conveyor 112 carrying bulk material 114i into a prompt gamma neutron activation analysis unit (PGNAA) 102 and bulk material 114o out of a dual-energy gamma attenuation unit (DGA) 104. In another embodiment the bulk material 114 flows first into the DGA 104 and then into the PGNAA 102. The PGNAA device 102 and the DGA device 104 communicate with a processor 106. Those skilled in the art will recognize that the bulk material 114 can be monitored by the PGNAA device 102 and the DGA device 104 in various manners, including the illustrated conveyor and a drop chute, without departing from the spirit and scope of the present invention.

Figure 2:
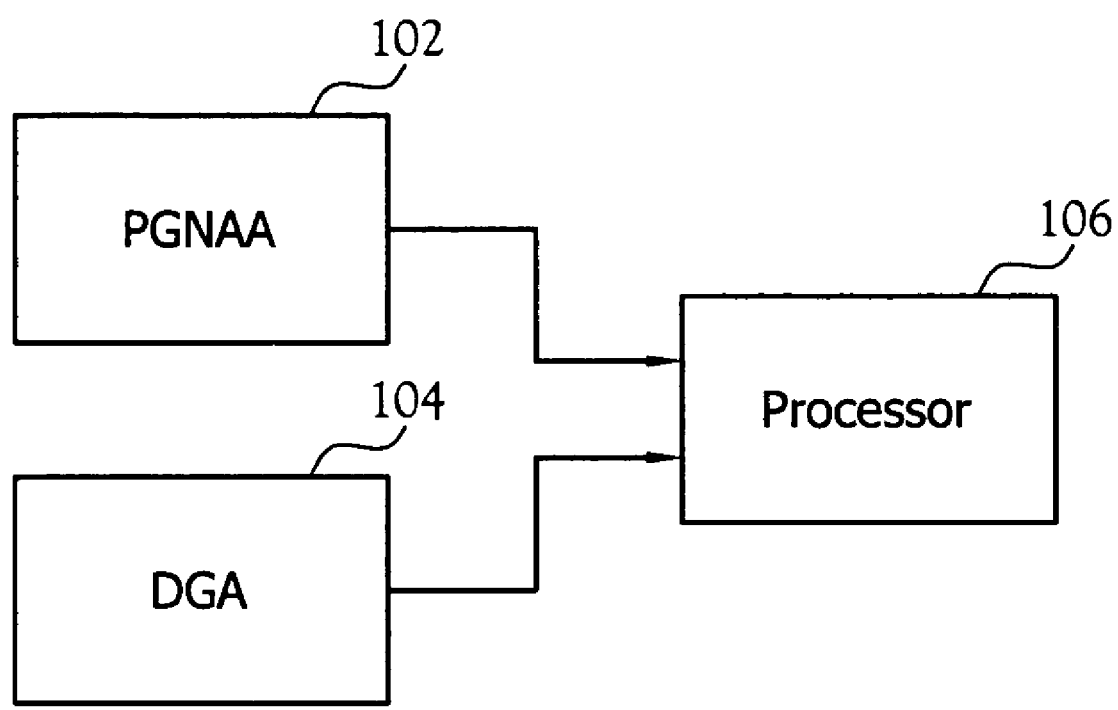
FIG. 2 is a block diagram of one embodiment of the apparatus.

FIG. 2 illustrates a block diagram showing the PGNAA device 102 and the DGA device 104 connected to a processor 106. As used herein, the processor 106 should be broadly construed to mean any computer or component thereof that executes software. The processor 106 includes a memory medium that stores software, a processing unit that executes the software, and input/output (I/O) units for communicating with external devices. Those skilled in the art will recognize that the memory medium associated with the processor 106 can be either internal or external to the processing unit of the processor without departing from the scope and spirit of the present invention. Further, in one embodiment, the processor 106 communicates with the PGNAA device 102 and the DGA device 104 via a network connection.

In one embodiment the processor 106 is a general purpose computer, in another embodiment, it is a specialized device for implementing the functions of the invention. Those skilled in the art will recognize that the processor 106 includes an input component, an output component, a storage component, and a processing component. The input component receives input from external devices, such as the PGNAA device 102, the DGA device 104, and a terminal device for operator input. The output component sends output to external devices, such as a printer, a display device, or another computer system or network. The storage component stores data and program code. In one embodiment, the storage component includes random access memory. In another embodiment, the storage component includes non-volatile memory, such as floppy disks, hard disks, and writeable optical disks. The processing component executes the instructions included in the software and routines.

Figure 3:
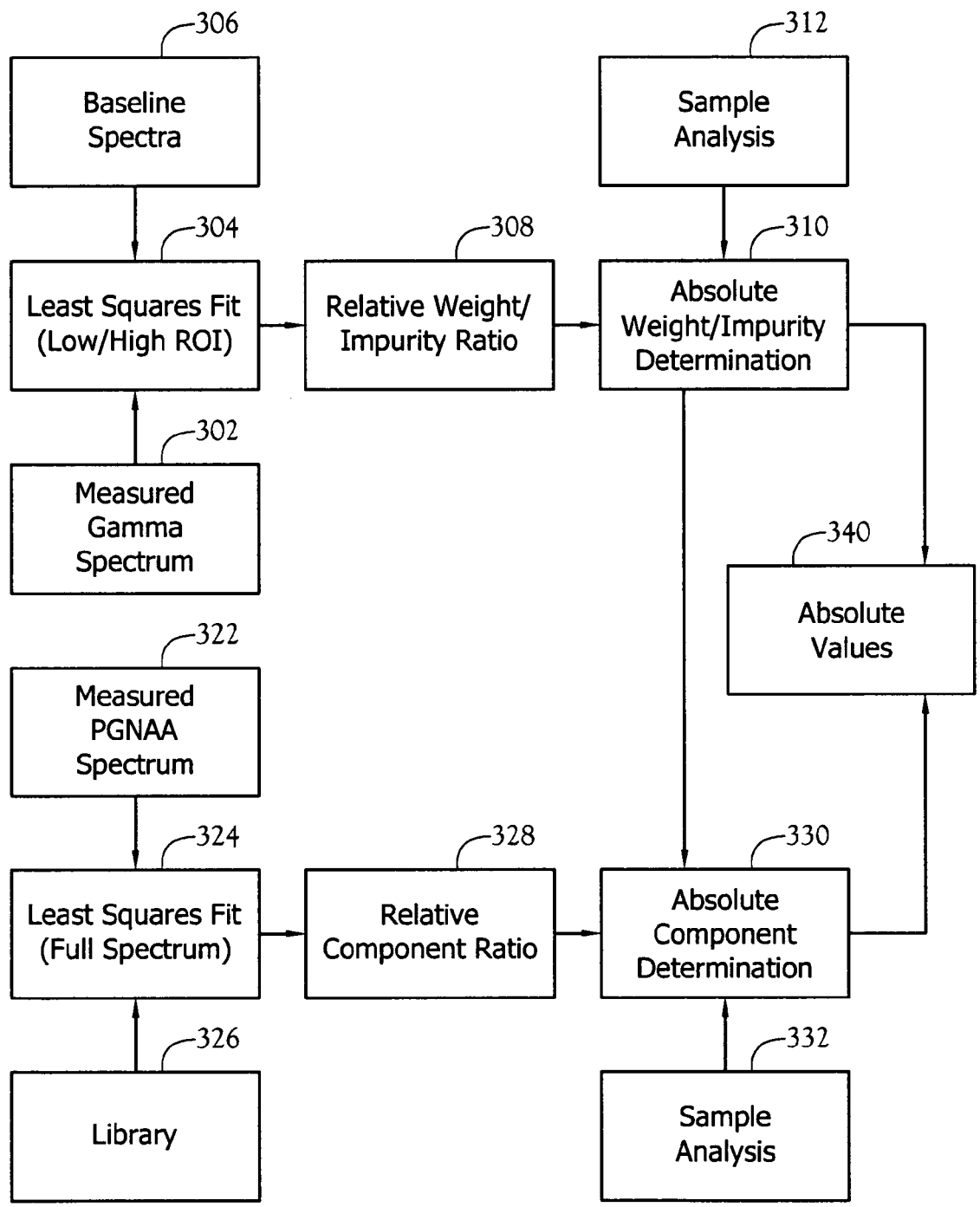
FIG. 3 is a flow diagram of one embodiment of the apparatus.

FIG. 3 illustrates a block diagram of one embodiment of the measurement system 10. The bulk material transport mechanism (conveyor in FIG. 1) 112 moves the bulk material 114 through the DGA device 104. Gamma rays emitted by the sources in the DGA device 104 are transmitted through the bulk material 114. These gamma rays interact with the bulk material 114 and are then captured by the detectors of the DGA device 104, in which the detected energy is converted into electronic signals. The electronic signals are analyzed by the processor 106 and compared with similar signals from a material free interrogation zone to give an indication of bulk material density and elemental content.

To perform the DGA measurement, gamma rays emitted by the DGA source are collected for a particular length of time to create an 'empty' or baseline spectrum 306. Then, the bulk material 114 is introduced to attenuate the gamma rays and again, a measured spectrum 302 is obtained. The specific low and high energy gamma ray attenuations are analyzed 304 and noted for this measured spectrum 302. The analysis 304 involves performing a least squares fit of the low and high regions of interest (ROI) of the measured gamma spectrum 302 with the baseline spectra 306. The ratio of the low energy gamma ray attenuation to the high energy gamma ray attenuation provides a relative measurement of the bulk material impurities, or a relative weight/impurity ratio 308. In one embodiment, impurities include silica, calcium, and sodium for coal as a bulk material 114.

The absolute weight/impurity determination 310 is performed using input from the DGA device 104. In particular, the relative weight/impurity ratio 308 and a sample analysis 312 are analyzed 310 to determine the absolute weight/impurity of the bulk material 114. In one embodiment, the sample analysis 312 is data produced by measuring several spectra that represent several different bulk material samples. The absolute/impurity determination 310 is performed by comparing the relative measurements 308 to the laboratory analyses of the samples 312. In other words, the absolute/impurity determination 310 relates the 'relative' measured values 308 to the absolute impurity values. It should also be noted here that the high energy attenuation can be used as a relative indication of material density (and therefore, weight) of the bulk material. By knowing the weight of the measured bulk material, the impurity content, and the relative impurity compositions, absolute weight components 310 for the elemental content of the impurities are calculated.

The bulk material transport mechanism 112 moves the bulk material 114 through the PGNAA device 102. Neutrons from the PGNAA device 102 interact with the bulk material 114 and produce gamma rays at varying energies that are captured by the detectors of the PGNAA device 102 in which the detected energy is converted into electronic signals. The electronic signals are analyzed by the processor 106 in light of the modeled PGNAA device 102 to determine the relative composition of elements in the material 328. The electronic signals are representative of a measured PGNAA spectrum 322.

The prompt gamma neutron activation analysis for determining the elemental content of the bulk material 114 is performed by developing a set of element based spectra 326, either by measurement or by modeling techniques, for each expected or known element to be measured. In the illustrated embodiment, this set of spectra is referred to as the spectra library 326. During measurement, the gamma rays from the activated bulk material are collected for some particular length of time to create a measured gamma spectrum 322. Then, a least-squares fit routine 324 of the full spectrum is used to fit a spectra from the library 326 to the measured spectra 322. The least squares fit of the spectra from the library 326 to the measured spectra 322 provides relative components of each library component required to best fit, from a least squares point of view, the measured spectra 322 and, therefore, provides a relative indication of the components making up the bulk material, or relative component ratio 328.

The absolute component determination 330 is performed using input from the DGA device 104 and the PGNAA device 102. In particular, the absolute weight/impurity ratio 310, the relative component ratio 328, and a sample analysis 332 are processed to determine the absolute components 330 of the bulk material 114. A known laboratory analysis 332 of the bulk material is related to the 'relative' least-squares values to arrive at a 'calibration' for future measurements. It must be remembered that the PGNAA measurement is capable of determining relative components 328 of the bulk material 114 that make up the bulk material impurities (e.g., the ash component of coal). To use the relative PGNAA measurements 328 in an absolute manner, the weight percentage of the impurities must be known. For this, the DGA portion of the measurement system is used because it is capable of determining a relative measurement of the bulk material impurities 308.

The end result of the absolute weight/impurity determination 310 and the absolute component determination 330 is to produce the absolute values 340 of the bulk material 114. The absolute values 340 include the weight and percent of the total for each component, including impurities. In another embodiment, the absolute values 340 include the weight and percent of the total for each element in the bulk material 114.

By accurately knowing the weight and impurity component of the bulk material 114 as well as the elemental content of the impurity component, mathematical models can be empirically created to provide additional or enhanced information on other components of the bulk material 114. For example, there are times when the DGA measurement is enhanced by knowing the elemental composition of the bulk material 114. Because the relative amount of each element in the bulk material 114 is based solely on the PGNAA portion of the instrument, it has no affect on the bulk material 114 impurity measurement. Therefore, the relative elemental composition of the impurity component of the bulk material 114 is used to enhance the DGA measurement for impurity component without affecting the elemental composition measurement.

Figure 4:
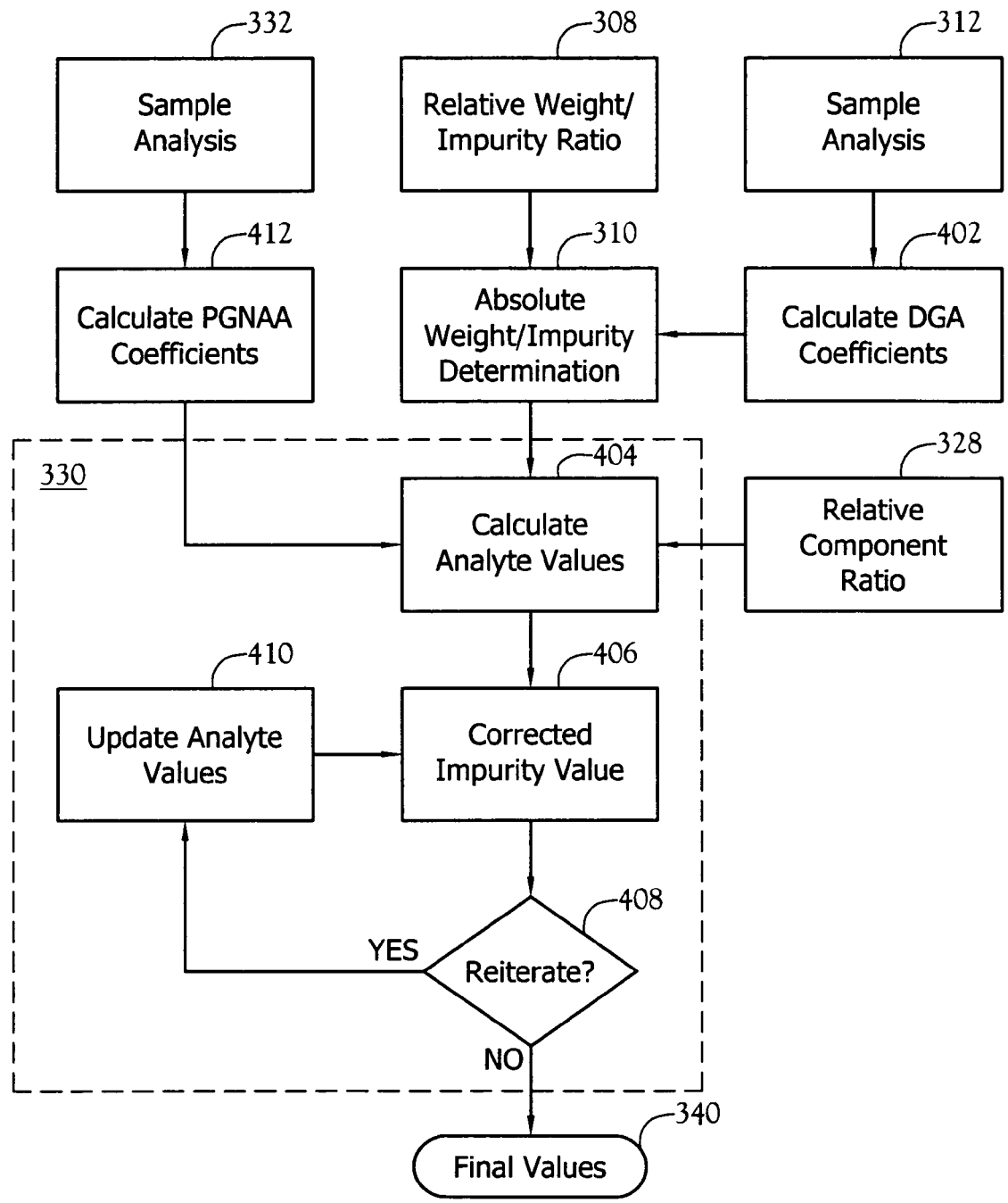
FIG. 4 is a flow diagram of one embodiment of the method of determining absolute values.

FIG. 4 illustrates one embodiment of the method of determining absolute values of the components of the bulk material 114. In one embodiment, the sample analysis 312 is performed by testing samples of bulk material 114 for impurities with laboratory or other special equipment to determine the impurity concentrations. These bulk material 114 samples are also run through the DGA device 104 to obtain measured relative weight/impurity ratios. The output of the DGA device 104 is a relative weight/impurity ratio 308. By measuring the relative weight/impurity ratios of the bulk material 114 samples with known impurities, the various coefficients for the polynomial equations used in determining absolute weight and impurity are refined and adjusted in the step of calculating the DGA coefficients 402. The sample analysis 312 and the step of calculating the DGA coefficients 402 are performed, in one embodiment, as a calibration, which is repeated as necessary to ensure accurate results. In one embodiment, the determination of the absolute weight and the determination of the absolute impurity 310 is based on the following equations:

$$Weight_{abs}=f(Weight_{rel})$$

$$Impurity_{abs}=f(Impurity_{rel})$$

In other words, the absolute weight ($Weight_{abs}$) is a function of the relative weight ($Weight_{rel}$) and the absolute impurity ($Impurity_{abs}$) is a function of the relative impurity ($Impurity_{rel}$). In one embodiment, these two equations are solved simultaneously to determine the absolute weight and impurity. In one embodiment, the absolute weight and impurity values are in units of percent weight.

For example, with coal being the bulk material 114, at least two samples with a known ash content are measured by the DGA device 104. The coefficients of the polynomial equations used in determining absolute weight and impurity are adjusted to curve-fit the equations with the relative weight/impurity ratio 308 measurements. After the DGA coefficients are determined 402, the absolute weight/impurity determination 310 of the bulk material 114 is made by applying each measured relative weight/impurity ratio 308 to the equations above. In one embodiment, the result from the absolute weight/impurity determination 310 is an absolute weight and an absolute impurity, in units of percent weight.

In one embodiment, the sample analysis 332 is performed by testing samples of bulk material 114 for the various impurities with laboratory or other special equipment to determine the concentrations of the impurities. These bulk material 114 samples are also run through the PGNAA device 102 to obtain measured relative impurity component ratios. The output of the PGNAA device 102 is a set of relative impurity component values 328. By measuring the relative impurity component ratios of the bulk material 114 samples with known impurities, the various coefficients for the polynomial equations used in determining absolute impurity analytes are refined and adjusted in the step of calculating the PGNAA coefficients 412. The sample analysis 332 and the step of calculating the PGNAA coefficients 412 are performed, in one embodiment, as a calibration, which is repeated as necessary to ensure accurate results.

After the absolute weight/impurity determination 310, the absolute values are combined with the relative component ratio 328 as provided by the PGNAA device 102 to calculate the analyte values 404. The output of the PGNAA device 102 includes the relative impurity component values 328. That is, using the above coal example, the bulk material impurity is ash, which includes analytes of silica, calcium, sodium, and other materials. In one embodiment, the determination of the absolute analyte values 404, in percent weight, for 1 to N analytes is based on the following series of equations:

$$Analyte\ 1_{abs}=f(Analyte\ 1_{rel}*Impurity_{abs})$$

$$Analyte\ 2_{abs}=f(Analyte\ 2_{rel}*Impurity_{abs})$$

$$Analyte\ 3_{abs}=f(Analyte\ 3_{rel}*Impurity_{abs})$$

$$Analyte\ N_{abs}=f(Analyte\ N_{rel}*Impurity_{abs})$$

The absolute impurity value ($Impurity_{abs}$) is corrected 406 by applying the absolute analyte values (Analyte labs to Analyte $N_{abs}$) calculated in step 404 to the absolute impurity value ($Impurity_{abs}$) determined in step 310. In one embodiment, the determination of a corrected impurity value 406 is based on the following equation:

$$Impurity_{abs}=f(previous\ Impurity_{abs})+f(Analyte\ 1_{abs})+f(Analyte\ 2_{abs})+f(Analyte\ 3_{abs})+\ldots+f(Analyte\ N_{abs})$$

The corrected absolute impurity value ($Impurity_{abs}$) is tested against the original, or previous, absolute impurity value (previous $Impurity_{abs}$) to determine if another iteration is necessary 408. In one embodiment, the corrected absolute impurity value ($Impurity_{abs}$) is subtracted from the original, or previous) absolute impurity value (previous $Impurity_{abs}$), and if the difference exceeds a specified amount, another iteration is necessary. The analyte values (Analyte $1_{abs}$ to Analyte $N_{abs}$) are recalculated, or updated, 410. The last calculated absolute impurity value (previous $Impurity_{abs}$) is applied to the relative analyte values (Analyte $1_{rel}$ to Analyte $N_{rel}$) to determine updated absolute analyte values 410. The updated absolute analyte values (Analyte $1_{abs}$ to Analyte $N_{abs}$) are then used to determine the corrected absolute impurity values 406. The loop represented by the steps for the corrected impurity value 406, reiterate 408, and update analyte values 410 is repeated until the absolute value of the difference between the last calculated impurity value (Impurity$_{abs}$) and the previous calculated impurity value (previous Impurity$_{abs}$) is less than a selected value that represents the acceptable error or tolerance value of the absolute impurity value (Impurity$_{abs}$). When no more iterations 408 are indicated, the final values 340 are output. In one embodiment, the final values 340 include the percent weight for each analyte, or element, in the bulk material 114.

In one embodiment, each of the functions identified above are performed by one or more software routines run by the processor 106. In another embodiment, one or more of the functions identified are performed by hardware and the remainder of the functions are performed by one or more software routines run by the processor 106.

The processor 106 executes software, or routines, for performing various functions. These routines can be discrete units of code or interrelated among themselves. Those skilled in the art will recognize that the various functions can be implemented as individual routines, or code snippets, or in various groupings without departing from the spirit and scope of the present invention. As used herein, software and routines are synonymous. However, in general, a routine refers to code that performs a specified function, whereas software is a more general term that may include more than one routine or perform more than one function. Those skilled in the art will recognize that it is possible to program a general-purpose computer or a specialized device to implement the invention.

The measurement system 10 includes several functions, both hardware and software. The system includes a function for communicating with the PGNAA 102 and the DGA 104. In one embodiment, the function of communicating is performed via a network connection between the processor 106 and the PGNAA 102 and the DGA 104. In another embodiment, the function of communication is performed by an electrical connection between the processor 106 and to the PGNAA 102 and the DGA 104. The system 10 includes a function for processing, which, in one embodiment, is performed by the processor 106.

The system 10 includes a function for determining at least one absolute impurity value of the bulk material 114, which, in one embodiment, is performed by the processor 106 executing a process for determining an absolute impurity value 310. In another embodiment, the function for determining at least one absolute impurity value is performed by the processor 106 executing a process for calculating DGA coefficients 402 from a sample analysis 312. The system 10 includes a function for determining at least one absolute weight value of the bulk material, which, in one embodiment, is performed by the processor 106 executing a process for determining an absolute weight value 310.

The system 10 includes a function for determining at least one absolute analyte value of the bulk material 114, which, in one embodiment, is performed by the processor 106 executing a process for determining an absolute component value 330. In another embodiment, the function for determining at least one absolute analyte value of the bulk material 114 is performed by the processor 106 executing a process for calculating analyte values 404 and calculating a corrected impurity value 406 in a loop in which the analyte values are updated 410. In another embodiment, the function for determining at least one absolute analyte value is performed by the processor 106 executing a process for calculating PGNAA coefficients 412 from a sample analysis 312.

The accurate determination of the elemental content of coal is important to the industry. Coal is composed of combustible materials (i.e., carbon and hydrogen) and non-combustible impurity materials (i.e., aluminum, silicon, etc.) which are typically referred to as ash. A PGNAA analyzer 102 can be used to great affect to determine the relative elemental composition 328 of the coal but can be biased in the determination of the ratio of combustible material to ash. A DGA device 104 can be used to great affect to determine the ratio 308 of combustible material to ash. However, the DGA device 104 can be biased by unexpected swings in the elemental composition in the bulk material 114. The elemental content of the bulk material 114 from the PGNAA device 102 can be used to account for the unexpected swings in the elemental composition of the bulk material 114 produced by the DGA device 104. And knowing the ratio 308 of combustible material to ash from the DGA analyzer 104 can be used to account for the true (as opposed to relative) elemental composition of the bulk material 114 determined by the PGNAA device 102.

Those skilled in the art will recognize that the example description for use of the invention in the coal industry can easily be extrapolated to uses in the analysis of other bulk materials, for example, other mining industries (i.e., bauxite, copper mining, etc.) and processing industries (i.e., cement, phosphate, etc.) without departing from the spirit and scope of the present invention.

From the foregoing description, it will be recognized by those skilled in the art that a measurement system 10 has been provided. The measurement system 10 combines the outputs from a PGNAA device 102 and a DGA device 104 to determine the absolute values 340 of the components of the bulk material 114. The outputs are combined, in one embodiment, by software executed by a processor 106 to produce an absolute impurity value and absolute analyte, or element, values for the bulk material. Because the PGNAA device 102 and the DGA device 104 monitor the bulk material 114 as a process flow, the absolute values produced reflect the process flow of bulk material 114.

While the present invention has been illustrated by description of several embodiments and while the illustrative embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicant's general inventive concept.

We claim:

1. An apparatus for measuring the absolute values of at least one component of a bulk material, said apparatus comprising:

a first data set representing a relative component ratio of the bulk material, said relative component ratio produced by a prompt gamma neutron activation analysis (PGNAA) device;

a second data set representing a relative weight/impurity ratio of the bulk material, said relative weight/impurity ratio produced by a dual-energy gamma attenuation (DGA) device; and a processor in communication with said PGNAA device and said DGA device, said processor programmed to execute a process including:
  receiving said relative weight/impurity ratio,
  receiving said relative component ratio,
  determining an absolute weight value from said relative weight/impurity ratio,
  determining an absolute impurity value from said relative weight/impurity ratio, and
  determining at least one absolute analyte value from said absolute impurity value and said relative component ratio.

2. The apparatus of claim 1 wherein said processor is programmed to execute said process further including determining a corrected impurity value from said at least one absolute analyte value.

3. The apparatus of claim 1 wherein said processor is programmed to execute said process further including determining a corrected impurity value from said at least one absolute analyte value, said step of determining said corrected impurity value repeating until an absolute difference between a newly calculated corrected impurity value and a previously calculated corrected impurity value is less than a specified value.

4. The apparatus of claim 1 wherein said process step of determining an absolute weight value from said relative weight/impurity ratio after said step (a) of providing for receiving said relative weight/impurity ratio, said process step of providing for determining said absolute weight value including
  receiving a sample data set from a sample analysis of at least one sample of the bulk material,
  receiving a test data set including a sample relative weight/impurity ratio from a measurement of said at least one sample of the bulk material, and
  calculating at least one DGA coefficient from said sample data set and said test data set.

5. The apparatus of claim 1 wherein said process step of determining said absolute impurity value includes
  receiving a sample data set from a sample analysis of at least one sample of the bulk material,
  receiving a test data set including a sample relative weight/impurity ratio from a measurement of said at least one sample of the bulk material, and
  calculating at least one DGA coefficient from said sample data set and said test data set.

6. The apparatus of claim 1 wherein said process step of determining said at least one absolute analyte value includes
  receiving a sample data set from a sample analysis of at least one sample of the bulk material,
  receiving a test data set including a sample relative component ratio from a measurement of said at least one sample of the bulk material, and
  calculating at least one PGNAA coefficient from said sample data set and said test data set.

7. The apparatus of claim 1 wherein at least one of said absolute weight value, said absolute impurity value, and said at least one absolute analyte value is in units of weight percent.

8. An apparatus for measuring the absolute values of at least one component of a bulk material, said apparatus comprising:
  a prompt gamma neutron activation analysis (PGNAA) device, said PGNAA device producing a relative component ratio of the bulk material;
  a dual-energy gamma attenuation (DGA) device, said DGA device producing a relative weight/impurity ratio of the bulk material; and
  a processor in communication with said PGNAA device and said DGA device, said processor programmed to execute a process including:
    receiving said relative weight/impurity ratio,
    receiving said relative component ratio,
    determining an absolute weight value from said relative weight/impurity ratio,
    determining an absolute impurity value from said relative weight/impurity ratio,
    determining at least one absolute analyte value from said absolute impurity value and said relative component ratio, and
    determining a corrected impurity value from said at least one absolute analyte value, said step of determining said corrected impurity value repeating until an absolute difference between a newly calculated corrected impurity value and a previously calculated corrected impurity value is less than a specified value.

9. A computer system for measuring the absolute values of at least one component of a bulk material, comprising:
  a memory medium for storing program code and a set of computer data;
  an input/output unit for communicating with a prompt gamma neutron activation analysis (PGNAA) device and a dual-energy gamma attenuation (DGA) device, said DGA device producing a relative weight/impurity ratio, said PGNAA device producing a relative component ratio; and
  a processing unit programmed to execute a process including:
    receiving said relative weight/impurity ratio,
    receiving said relative component ratio,
    determining an absolute impurity value from said relative weight/impurity ratio, and
    determining at least one absolute analyte value from said absolute impurity value and said relative component ratio.

10. The apparatus of claim 9 wherein said process executed by said processing unit further includes determining an absolute weight value from said relative weight/impurity ratio.

11. The apparatus of claim 9 wherein said process executed by said processing unit further includes determining an absolute weight value from said relative weight/impurity ratio, said process step of providing for determining said absolute weight value including
  receiving a first data set from a sample analysis of at least one sample of the bulk material,
  receiving a second data set including a sample relative weight/impurity ratio from a measurement of said at least one sample of the bulk material, and
  calculating at least one DGA coefficient from said first data set and said second data set.

12. The apparatus of claim 9 wherein said processing unit is programmed to execute said process further including determining a corrected impurity value from said at least one absolute analyte value.

13. The apparatus of claim 9 wherein said processing unit is programmed to execute said process further including determining a corrected impurity value from said at least one absolute analyte value, said step of determining said corrected impurity value repeating until an absolute difference between a newly calculated corrected impurity value and a previously calculated corrected impurity value is less than a specified value.

14. The apparatus of claim 9 wherein said process step of determining said absolute impurity value includes
receiving a sample data set from a sample analysis of at least one sample of the bulk material,
receiving a test data set including a sample relative weight/impurity ratio from a measurement of said at least one sample of the bulk material, and
calculating at least one DGA coefficient from said sample data set and said test data set.

15. The apparatus of claim 9 wherein said process step of determining said at least one absolute analyte value includes
receiving a sample data set from a sample analysis of at least one sample of the bulk material,
receiving a test data set including a sample relative component ratio from a measurement of said at least one sample of the bulk material, and
calculating at least one PGNAA coefficient from said sample data set and said test data set.

16. The apparatus of claim 9 wherein at least one of said absolute impurity value and said at least one absolute analyte value is in units of weight percent.

17. An apparatus for measuring the absolute values of at least one component of a bulk material, said apparatus comprising:
a means for communicating with a prompt gamma neutron activation analysis (PGNAA) device and a dual-energy gamma attenuation (DGA) device;
a means for processing; and
a means for determining at least one absolute impurity value of the bulk material.

18. The apparatus of claim 17 further including a means for determining at least one absolute analyte value of the bulk material.

19. A method in a computer system for measuring the absolute values of at least one component of a bulk material, the method comprising:
(a) providing for receiving a relative weight/impurity ratio from a dual-energy gamma attenuation (DGA) device monitoring the bulk material;
(b) providing for receiving a relative component ratio from a prompt gamma neutron activation analysis (PGNAA) device monitoring the bulk material;
(c) providing for determining an absolute impurity value from said relative weight/impurity ratio; and
(d) providing for determining at least one absolute analyte value from said absolute impurity value and said relative component ratio.

20. The method of claim 19 further including a step of providing for determining an absolute weight value from said relative weight/impurity ratio after said step (a) of providing for receiving said relative weight/impurity ratio.

21. The method of claim 19 further including a step of providing for determining an absolute weight value from said relative weight/impurity ratio after said step (a) of providing for receiving said relative weight/impurity ratio, said process step of providing for determining said absolute weight value including
providing for receiving a first data set from a sample analysis of at least one sample of the bulk material,
providing for receiving a second data set including a sample relative weight/impurity ratio from a measurement of said at least one sample of the bulk material, and
providing for calculating at least one DGA coefficient from said first data set and said second data set.

22. The method of claim 19 further including a step of providing for determining a corrected impurity value from said at least one absolute analyte value after said step (d) of providing for determining said at least one absolute analyte value.

23. The method of claim 19 further including a step of providing for determining a corrected impurity value from said at least one absolute analyte value after said step (d) of providing for determining said at least one absolute analyte value, said step of determining said corrected impurity value repeating until an absolute difference between a newly calculated corrected impurity value and a previously calculated corrected impurity value is less than a specified value.

24. The method of claim 19 wherein said process step (c) of providing for determining said absolute impurity value includes providing for receiving a first data set from a sample analysis of at least one sample of the bulk material,
providing for receiving a second data set including a sample relative weight/impurity ratio from a measurement of said at least one sample of the bulk material, and
providing for calculating at least one DGA coefficient from said first data set and said second data set.

25. The method of claim 19 wherein said process step (d) of providing for determining said at least one absolute analyte value includes
providing for receiving a first data set from a sample analysis of at least one sample of the bulk material,
providing for receiving a second data set including a sample relative component ratio from a measurement of said at least one sample of the bulk material, and
providing for calculating at least one PGNAA coefficient from said first data set and said second data set.

26. The method of claim 19 wherein at least one of said absolute impurity value and said at least one absolute analyte value is in units of weight percent.

27. Computer readable media tangibly embodying a program of instructions executable by a computer to perform a method of measuring the absolute values of at least one component of a bulk material, said method comprising:
(a) providing for receiving a relative weight/impurity ratio from a dual-energy gamma attenuation (DGA) device monitoring the bulk material;
(b) providing for receiving a relative component ratio from a prompt gamma neutron activation analysis (PGNAA) device monitoring the bulk material;
(c) providing for determining an absolute impurity value from said relative weight/impurity ratio; and
(d) providing for determining at least one absolute analyte value from said absolute impurity value and said relative component ratio.

28. The media of claim 27 further including a step of providing for determining an absolute weight value from said relative weight/impurity ratio after said step (a) of providing for receiving said relative weight/impurity ratio.

29. The media of claim 27 further including a step of providing for determining an absolute weight value from said relative weight/impurity ratio after said step (a) of providing for receiving said relative weight/impurity ratio, said process step of providing for determining said absolute weight value including
providing for receiving a first data set from a sample analysis of at least one sample of the bulk material, providing for receiving a second data set including a sample relative weight/impurity ratio from a measurement of said at least one sample of the bulk material, and providing for calculating at least one DGA coefficient from said first data set and said second data set.

30. The media of claim 27 further including a step of providing for determining a corrected impurity value from said at least one absolute analyte value after said step (d) of providing for determining said at least one absolute analyte value.

31. The media of claim 27 including a step of providing for determining a corrected impurity value from said at least one absolute analyte value after said step (d) of providing for determining said at least one absolute analyte value, said step of providing for determining said corrected impurity value repeating until an absolute difference between a newly calculated corrected impurity value and a previously calculated corrected impurity value is less than a specified value.

32. The media of claim 27 wherein said process step (c) of providing for determining said absolute impurity value includes providing for receiving a first data set from a sample analysis of at least one sample of the bulk material, providing for receiving a second data set including a sample relative weight/impurity ratio from a measurement of said at least one sample of the bulk material, and providing for calculating at least one DGA coefficient from said first data set and said second data set.

33. The media of claim 27 wherein said process step (d) of providing for determining said at least one absolute analyte value includes providing for receiving a first data set from a sample analysis of at least one sample of the bulk material, providing for receiving a second data set including a sample relative component ratio from a measurement of said at least one sample of the bulk material, and providing for calculating at least one PGNAA coefficient from said first data set and said second data set.

34. The media of claim 27 wherein at least one of said absolute impurity value and said at least one absolute analyte value is in units of weight percent.

* * * * *